US010444543B2

(12) United States Patent
Thompson

(10) Patent No.: US 10,444,543 B2
(45) Date of Patent: Oct. 15, 2019

(54) CONTROL DEVICE RESPONSIVE TO LID FISSURE WIDTH

(71) Applicant: OneFocus Vision, Inc., Fernandina Beach, FL (US)

(72) Inventor: Vance Thompson, Sioux Falls, SD (US)

(73) Assignee: OneFocus Vision, Inc., Fernandina Beach, FL (US)

( * ) Notice: Subject to any disclaimer, the term of this patent is extended or adjusted under 35 U.S.C. 154(b) by 0 days.

(21) Appl. No.: 15/413,727

(22) Filed: Jan. 24, 2017

(65) Prior Publication Data
US 2017/0131570 A1 May 11, 2017

Related U.S. Application Data

(63) Continuation of application No. PCT/US2015/043326, filed on Jul. 31, 2015.
(Continued)

(51) Int. Cl.
G02C 7/08 (2006.01)
G02C 7/04 (2006.01)
(Continued)

(52) U.S. Cl.
CPC ............ *G02C 7/085* (2013.01); *A61F 9/0017* (2013.01); *B29D 11/00028* (2013.01);
(Continued)

(58) Field of Classification Search
CPC ........ G02C 7/043; G02C 7/048; G02C 7/049; G02C 7/085; G02C 7/04; G02C 7/041; G02C 7/083
See application file for complete search history.

(56) References Cited

U.S. PATENT DOCUMENTS 3,102,157 A 8/1963 Gamber
3,591,264 A 7/1971 Robert et al.
(Continued)

FOREIGN PATENT DOCUMENTS

EP 2639626 A2 9/2013
WO WO-9110154 A1 7/1991
(Continued)

OTHER PUBLICATIONS

International search report with written opinion dated Nov. 4, 2015 for PCT/US2015/043326.
(Continued)

*Primary Examiner* — Jordan M Schwartz
(74) *Attorney, Agent, or Firm* — Fisherbroyles LLP; John Shimmick

(57) ABSTRACT

An accommodating contact lens comprises a control device, which comprises one or more eyelid engagement structures. The eyelid engagement structures are configured to move with the eyelid relative to the contact lens. The eyelid engagement structure is coupled to the eyelid and to the accommodating contact lens, which may comprise a fluidic module having inner and outer fluid reservoirs. The eyelid engagement structure is configured to respond to the narrowing or widening of the eyelid fissure, moving a fluid in or out of the inner reservoir to accommodate near or far vision.

11 Claims, 6 Drawing Sheets

Related U.S. Application Data

(60) Provisional application No. 62/031,305, filed on Jul. 31, 2014.

(51) Int. Cl.
*A61F 9/00* (2006.01)
*B29D 11/00* (2006.01)
*G02B 3/14* (2006.01)

(52) U.S. Cl.
CPC .. *B29D 11/00048* (2013.01); *B29D 11/00134* (2013.01); *G02B 3/14* (2013.01); *G02C 7/04* (2013.01); *G02C 7/049* (2013.01); *G02C 7/083* (2013.01); *B29K 2825/06* (2013.01); *G02C 7/048* (2013.01); *G02C 2202/18* (2013.01)

(56) References Cited

U.S. PATENT DOCUMENTS

| | | | | |
|---|---|---|---|---|
| 4,640,594 | A * | 2/1987 | Berger | G02C 7/04 351/159.04 |
| 5,141,301 | A | 8/1992 | Morstad | |
| 5,764,339 | A * | 6/1998 | Horton | G02C 7/041 351/159.02 |
| 9,910,296 | B2 | 3/2018 | Harant | |
| 2003/0020477 | A1* | 1/2003 | Goldstein | H02J 17/00 324/415 |
| 2007/0273825 | A1* | 11/2007 | Legerton | B29D 11/00048 351/159.78 |
| 2008/0097600 | A1* | 4/2008 | Hare | G02C 7/041 623/6.37 |
| 2008/0231799 | A1 | 9/2008 | Iuliano | |
| 2012/0268712 | A1 | 10/2012 | Egan et al. | |
| 2013/0102921 | A1* | 4/2013 | Saurer | A61B 3/16 600/558 |
| 2013/0242255 | A1 | 9/2013 | Caldarise et al. | |
| 2015/0157591 | A1* | 6/2015 | Zhu | A61K 38/13 514/8.9 |
| 2015/0370093 | A1 | 12/2015 | Waite | |
| 2016/0004098 | A1 | 1/2016 | Waite | |
| 2016/0018671 | A1 | 1/2016 | Waite | |
| 2016/0377887 | A1 | 12/2016 | Waite | |
| 2017/0131571 | A1 | 5/2017 | Waite | |
| 2017/0258320 | A1* | 9/2017 | Abreu | A61B 3/1241 |
| 2018/0173010 | A1 | 6/2018 | Harant | |

FOREIGN PATENT DOCUMENTS

| | | |
|---|---|---|
| WO | WO-2008115251 A1 | 9/2008 |
| WO | WO-2014117173 A2 | 7/2014 |
| WO | WO-2014120928 A2 | 8/2014 |
| WO | 2014161002 A2 | 10/2014 |
| WO | WO-2015095891 A1 | 6/2015 |
| WO | 2016019346 | 2/2016 |
| WO | 2016019351 | 2/2016 |
| WO | 2016019359 | 2/2016 |
| WO | WO-2016019359 A1 | 2/2016 |
| WO | 2017083770 | 5/2017 |
| WO | 2017083771 | 5/2017 |
| WO | 2017083774 | 5/2017 |
| WO | 2018089699 | 5/2018 |

OTHER PUBLICATIONS

European search report with written opinion dated Feb. 19, 2018 for EP Application No. 15827121.
Copending U.S. Appl. No. 15/972,900, filed May 7, 2018.
Copending U.S. Appl. No. 15/988,738, filed May 24, 2018.
Shaw, Alyra J.B., "Eyelid Pressure on the Cornea," Thesis, Institute of Health of Biomedical Innovation, School of Optometry, Queensland University of Technology, Brisbane, Australia (2009).

* cited by examiner

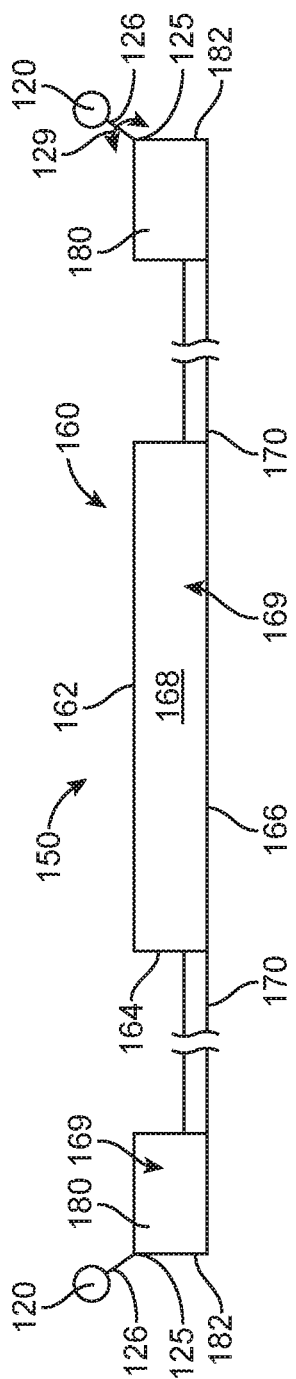
FIG. 5
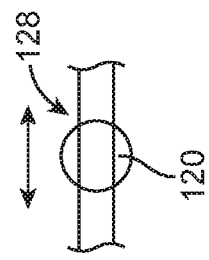
FIG. 7
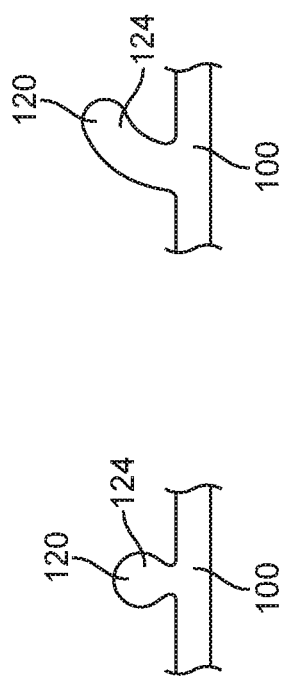
FIG. 6B
FIG. 6A

CONTROL DEVICE RESPONSIVE TO LID FISSURE WIDTH

CROSS-REFERENCE

The present application is a continuation of PCT Application Ser. No. PCT/US2015/043326, filed Jul. 31, 2015, entitled "Control Device Responsive to Lid Fissure Width", which claims priority to U.S. Provisional Application Ser. No. 62/031,305, filed on Jul. 31, 2014, entitled "Control Device Responsive to Lid Fissure Width", the entire disclosures of which are incorporated herein by reference.

This subject matter of the present application is related to the following patent applications: PCT/US2014/013427, filed on 28 Jan. 2014, entitled "Accommodating Soft Contact Lens"; U.S. Application Ser. No. 61/757,457, filed on Jan. 28, 2013, entitled "An Accommodating Soft Contact Lens"; PCT/US2014/013859, filed on Jan. 30, 2014, entitled "Manufacturing Process of an Accommodating Contact Lens"; U.S. Application Ser. No. 61/758,416, filed on Jan. 30, 2013, entitled "Manufacturing Process of an Accommodating Soft Contact Lens"; U.S. Application Ser. No. 61/857,462, filed Jul. 23, 2013, entitled "Manufacturing Process of an Accommodating Soft Contact Lens II"; PCT/US2014/071988, filed on Dec. 22, 2014, entitled "Fluidic Module For Accommodating Soft Contact Lens"; U.S. Application Ser. No. 61/919,691, filed on Dec. 20, 2013, entitled "Fluidic Meniscus Module for Accommodating Soft Contact Lens"; U.S. Provisional Application Ser. No. 62/031,290, filed on Jul. 31, 2014, entitled "Fluidic Meniscus Module for Accommodating Soft Contact Lens"; and U.S. Application Ser. No. 62/031,324, filed Jul. 31, 2014, entitled "Sacrificial Molding Process for an Accommodating Contact Lens", the entire disclosures of which are incorporated herein by reference.

BACKGROUND OF THE INVENTION

Prior methods and apparatus for treating eyes can be less than ideal in at least some respects.

Although it has been proposed to treat presbyopia with accommodating contact lenses, the prior accommodating contact lenses can provide less than ideal results in at least some instances. For example, work in relation to embodiments suggests that users wearing such lenses would like to have improved control of the lens, and that the amounts of accommodation provided with the prior lenses can be less than ideal in at least some instances. For example, it could be helpful to allow the user to accommodate to near vision when looking horizontally or up. Also, movement and alignment of the corrective near vision zone with the pupil can be less than ideal in at least some instances with at least some of the prior accommodating contact lenses.

Although drug eluting contact lenses have been proposed, drug eluting lenses may provide less than ideal amounts of the drug, and the control of the rate of release of the drug can be less than ideal in at least some instances.

In light of the above, it would be helpful to provide improved accommodating contact lenses and improved methods and apparatus for drug delivery. Ideally, the improved methods and apparatus would provide one or more of improved user control of the contact lens, provide improved user control of accommodation, provide improved alignment with the pupil, or improved user control of drug delivery.

SUMMARY

Embodiments provide improved user control of apparatus coupled to the user such as contact lenses. The control device can be configured in one or more of many ways to respond to the width of the palpebral fissure of the eye. The control based on the palpebral fissure of the eye has the advantage of allowing the user to control the apparatus with movements that can be independent of eye movement. With embodiments comprising the adjustable focus lenses such as eye glasses and contact lenses, the control in response to the width of the palpebral fissure has the advantage of allowing the user to adjust focus with a squint of each eye. The adjustable focus in response to squint of the eye has the advantage of allowing the user to control focus independently of the direction of gaze and head angle.

In many embodiments, the control device comprises a plurality of eyelid engagement structures shaped to engage one or more eyelids of the user that define the palpebral fissure. The eyelid engagement structures can move closer to each other when the eyelids close and farther from each other when the eyelids separate. In many embodiments, each of the eyelid engagement structures comprises a surface shaped to contact the eyelid. In many embodiments, the control apparatus comprises an extension such as a lever that allows the eyelid to move readily with leverage. The control apparatus may comprise a resilient structure that resiliently deforms in response to movement of the eyelid engagement structures. The resilient structure may comprise a deflectable lever such as a spring, or a resiliently deformable structure such as a wall of a reservoir. The resilient coupling with leverage of the eyelid engagement structures decreases resistance of the eyelid engagement structures to movement, and allows natural movement of the eyelids such that the eyelids can blink and perform natural functions such as providing tears and nutrients to the eye.

The control device can be coupled to one or more of many apparatus such as accommodating eye glasses, contact lenses, smart contact lenses, therapeutic drug delivery reservoirs, accommodating contact lenses, artificial pupils, accommodating intraocular lenses and computer interfaces and visual displays. The control device can be coupled to the apparatus in one or more of many ways, such as with mechanical coupling, a mechanical linkage, wired or wireless connections, electromagnetic and optical coupling, and the control device may comprise coupling circuitry. The eyeglasses may comprise eyeglasses having variable optical power. The accommodating contact lens may comprise a fluidic contact lens or an electro optical accommodating contact lens.

In many embodiments, the control device is integrated with a fluidic accommodating contact lens. The contact lens may comprise one or more eyelid engagement structures configured to engage the eyelid and move with one or more eyelids relative to the contact lens in order to control the contact lens. The movement of the eyelid engagement structure relative to the contact lens can allow the user to control a function of the contact lens, such as accommodation, and maintain a position of the contact lens on the eye. In many embodiments, the eyelid engagement structure is shaped to engage the eyelid and move with the eyelid in response to the user narrowing of the eyelid fissure. The eyelid engagement structure can be shaped in one or more of many ways to engage the eyelid. In many embodiments, the eyelid engagement structure protrudes from the contact lens body in order to engage the eyelid. The eyelid engagement structure can be shaped in one or more of many ways and may comprise one or more of a ball structure, an involute structure, a u-shaped structure, or a concave structure. The eyelid engagement structure can be configured to engage one or more puncta of the eyelid, and may comprise a protrusion sized and shaped to fit within a punctum.

The one or more eyelid engagement structures can be configured in one or more of many ways to engage the eyelid, and may comprise a single eyelid engagement structure, or a plurality of eyelid engagement structures. In many embodiments, a plurality of eyelid engagement structures are arranged on the contact lens at locations to engage opposing eyelids, such that the user can readily control the eyelid engagement structures for accommodation, or therapeutic agent delivery, or both. The contact lens may comprise a plurality of eyelid engagement structures to engage each of the upper lid and the lower lid of the eye, for example.

The one or more eyelid engagement structures can be coupled to the contact lens in one or more of many ways. In many embodiments, the eyelid engagement structures are coupled to the contact lens with a coupling structure that transmits force from the portion of the eyelid engagement structure that contacts the eyelid to the contact lens. The coupling structure may comprise one of an extension, a lever arm, a slider or a deflectable extension. In many embodiments, the coupling structure extends outwardly from a reservoir of the contact lens to the eyelid engagement structure. The deflectable extension may comprise a wing extending from a reversibly deformable reservoir disposed on the contact lens body, and the wing may comprise an eyelid engaging portion shaped to receive the eyelid.

In many embodiments, the coupling structure comprises a deflectable structure that urges against a deformable structure such as a reversibly deformable reservoir, in order to release a fluid from the reservoir when the member urges against the reservoir. The deflection of the deflectable member may allow the eyelid engagement structure to move quickly with the one or more eyelids with decreased resistance, and apply force to the deformable reservoir in order to release fluid from the reservoir. One or more channels can be coupled to the reservoir in order to release fluid from the one or more channels at a rate slower than corresponding movement of the eyelid. This release rate that is slower than the movement of the eyelid allows the eyelid to move quickly with blinks of the eye without moving substantial amounts of fluid from the reservoir. This delay in fluid movement is well suited for use with accommodating contact lenses, in which a user may want to blink while looking at distant objects without having a change in focus. This arrangement can also be used with drug delivery, and the reservoir may comprise a therapeutic agent.

The eyelid engagement structures can be coupled to the reservoir with one or more components of a preformed module encapsulated in a contact lens. The module of the contact lens may comprise a module suitable for embedding in a soft contact lens material such as a silicone hydrogel material. The module may comprise a pre-formed structural support capable of being placed in a contact lens mold. The module may comprise one or more anchors to retain the module in the soft contact lens material. The module may comprise one or more components to provide accommodation or drug delivery with the contact lens, and combinations thereof In many embodiments, the contact lens comprises an accommodating contact lens. The accommodating contact lens may comprise an inner, central optical fluid reservoir coupled to a peripheral or outer fluid reservoir, with a channel extending therebetween. The eyelid engagement structure can engage the eyelid and provide a transfer of fluid from the outer reservoir to the inner optical reservoir in order to provide optical correction for near vision. When the eyelids open, the inner optical reservoir returns fluid to the outer reservoir. Additional fluid in the inner reservoir can provide additional optical power in response to movement of the eyelid. In many embodiments, the eyelid engagement structure comprises a protrusion extending from a contact lens body, and movement of the eyelid engagement structure urges fluid to the inner optical fluid reservoir as the eyelids come together.

Alternatively or in combination, the contact lens may comprise a reservoir of a therapeutic agent coupled to the eyelid engagement structure in order to release amounts of therapeutic agent in response to movement of the eyelid engagement structures. The contact lens can be provided with a release mechanism that releases an amount of therapeutic agent in response to a plurality of inward and outward cycles of the eyelid engagement structure in order to provide an appropriate amount of therapeutic agent. The therapeutic agent may comprise one or more of many known therapeutic agents such as one or more of artificial tears, or glaucoma medication.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5 shows a side view of an accommodating contact lens module, in accordance with embodiments;

FIG. 6A shows an eyelid engagement structure comprising a ball shaped engagement structure, in accordance with embodiments;

FIG. 6B shows an eyelid engagement structure comprising an involute structure shaped to receive at least a portion of the eyelid, in accordance with embodiments;

FIG. 7 shows an eyelid engagement structure comprising a slider structure, in accordance with embodiments.

DETAILED DESCRIPTION

Figure 1:
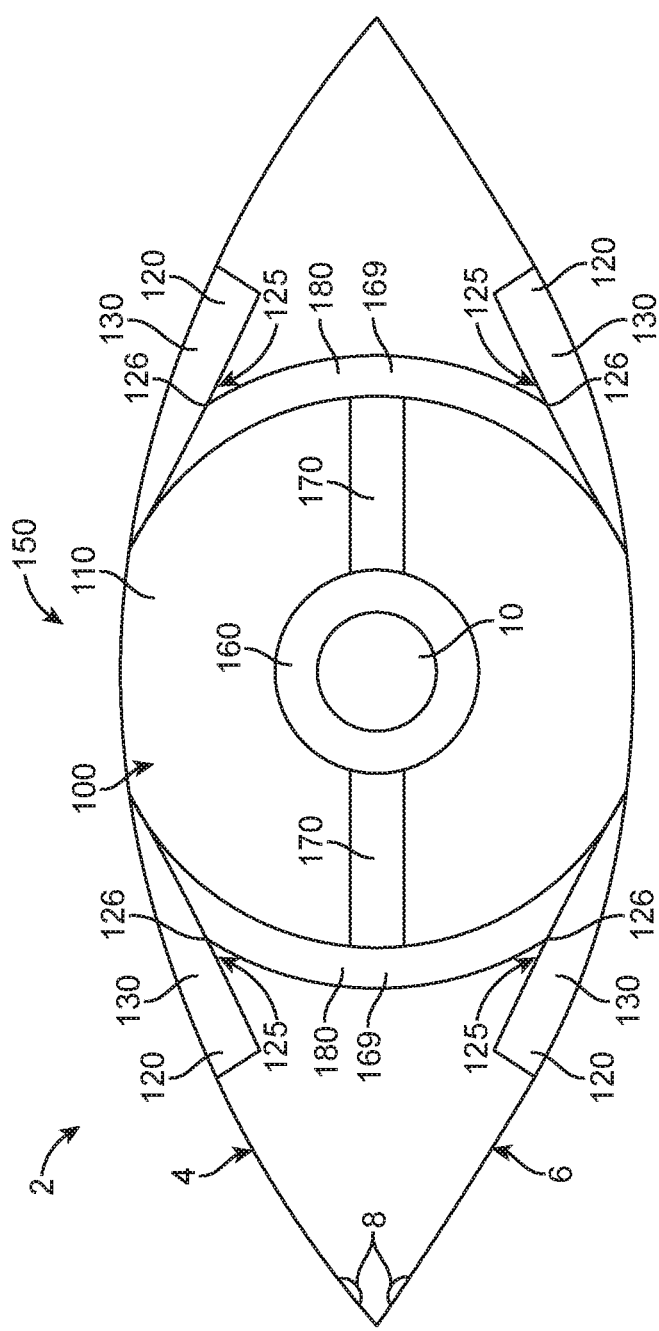
FIG. 1 shows an accommodating contact lens comprising eyelid engagement structures, in accordance with embodiments.

Embodiments of the present disclosure provide improve methods and apparatus for combination with contact lenses and therapeutic shields of the eye. The embodiments as disclosed herein are well suited with one or more of many prior art lenses and shields such as silicone hydrogel lenses and collagen lenses. The embodiments as disclosed herein are suitable for combination with fluidic contact lenses, such as accommodating contact lenses and contact lenses for drug delivery, for example. The embodiments as disclosed herein are well suited for combination with accommodating contact lenses comprising a module composed of an optically transmissive material. The moveable eyelid engagement structure as disclosed herein can be combined with one or more optically transmissive structures embedded in the contact lens in order to provide stability to the contact lens and inhibit tearing of the contact lens with coupling of the moveable eyelid engagement structure with one or more optically transmissive structures embedded in the contact lens, for example. The structure embedded in the contact lens may comprise one or more optically transmissive structures within an optical zone of the contact lens, for example, such as one or more anchoring structures to anchor the module within the contact lens, which may comprise a soft contact lens such as a silicone hydrogel lens or a collagen shield, for example.

In many embodiments, the methods and apparatus as disclosed herein are combined with an accommodating contact lens as described in U.S. Pat. App. Ser. No. 61/757, 457, filed on 28 Jan. 2013, entitled "An accommodating soft contact lens"; PCT Pat. App. No. PCT/US2014/013427, filed Jan. 28, 2014, entitled, "Accommodating soft contact lens"; U.S. Pat. App. Ser. No. 61/857,462, filed on Jul. 23, 2013, entitled "Manufacturing process of an accommodating contact lens"; and PCT Pat. App. No. PCT/US2014/013859, filed 30 Jan. 2014, entitled "Manufacturing process of an accommodating soft contact lens"; the entire disclosures of which are incorporated herein by reference.

Liquid

In many embodiments, a fluidic liquid material can flow into a space over the visual axis for reading when mechanically stimulated, for example with a force of the eyelid. When the mechanical force of the eyelid is not in action, the fluidic material can flow back to an optical fluid reservoir thereby allowing good distance vision. In many embodiments, the reservoir is located on the lateral aspect of the contact lens device, for example at least a portion of the reservoir can be located at 3 o'clock and 9 o'clock positions with respect to the contact lens. The reservoir can be located at one or more of many additional and alternative locations, such as in the peripheral contact lens body. In many embodiments a fluidic channel provides a path for fluidic communication extending from the reservoir to the central optic and back. Alternatively or in combination with the accommodating contact lens embodiments, a reservoir can be provided to deliver a therapeutic agent in response to eyelid movements. In many embodiments the liquid comprises an index of refraction similar to the soft contact lens material, in order to inhibit optical artifacts.

Control Device

In many embodiments, a control device comprises one or more eyelid engagement structures that couple eyelid movement and/or eyelid fissure narrowing with fluid movement from the fluid reservoir to the central optic. In many embodiments, narrowing of the lid fissure provides a force to stimulate reading. Work in relation to embodiments suggests that the fissures of the eyelid opening narrow when the eye transitions from far vision to near vision. The embodiments disclosed herein can provide the user with an easy way to adjust the focus of the lens. In many embodiments, the squint that a person can use will induce even more optical power to look at even smaller things. The embodiments disclosed herein can be configured to provide a linear response between lid narrowing and optical power, with more lid fissure narrowing providing more optical power. When the fissure opens, the lens adjusts to far vision.

In many embodiments, the eyelid engagement structure comprises wing structures that have at least some flexibility to them. When the eyelid fissure narrows, the wings can move inwardly toward the center of the lens and create a compressive force in the outer reservoir chambers, so as to urge the fluid toward the inner optical reservoir. When this force goes back toward near zero (no fissure narrowing), the fluid moves back to the reservoir and decreases the optical power of the central optical add lens.

In many embodiments, an inwardly curved structure near the borders of the reservoir is provided. The slightly stiff and resilient outer border can curve inwardly when the eyelids compress slightly, such that the curve can move in and compress the contents in this outer chamber towards the inner, central optic. Upon eyelid widening, the eyelids release the curved section and it will naturally go back into its unloaded position and draw the fluid from the optic to the reservoir for good far vision. The superior and inferior border of the reservoir could also be curve in for the same reason.

The control device can be configured in one or more of many ways for the user to stimulate the flow of fluid from the optical reservoir to the central optic. In many embodiments, the user can simply look down, as looking down can narrow the eyelid opening fissure. Alternatively or in combination, the user can purposefully narrow the lid fissure through a squint in order to provide near vision.

FIG. 1 shows an accommodating contact lens 100 comprising an eyelid engagement structure 120. The eyelid engagement structure comprises extensions such as wing structures 130 that are coupled to the upper lid 4 and lower lid 6 of an eye 2, to move the eyelid relative to the contact lens. The extensions may comprise one or more of arms, levers, or wings, for example. The accommodating contact lens 100 comprises a soft contact lens material 110 and a fluidic accommodation module 150. The fluidic module comprises an inner central optical fluid reservoir 160 disposed over the pupil 10, one or more peripheral or outer fluid reservoirs 180, one or more channels 170, and coupling structures 126 to couple the fluidic module to the eyelid engagement structures.

As described herein, when the eyelids move to narrow the eyelid fissure, the wings can move inwardly toward the center of the lens and transmit a compressive force through the coupling structures to the chambers of the outer reservoirs. This compressive force urges the fluid 169 in the outer reservoir to move through the channels towards the inner optical reservoir, increasing the optical power of the central add lens. When the eyelids open and the eyelid fissure widens, this force goes back toward zero, and the fluid moves back to the reservoir and decreases the optical power of the central add lens.

In embodiments, the wings comprise lever arms configured to provide force to the reservoir. This leveraged force to the reservoir can decrease the resistance of the eyelid engagement structure to forces of the eyelid and provide improved user comfort.

Figure 2:
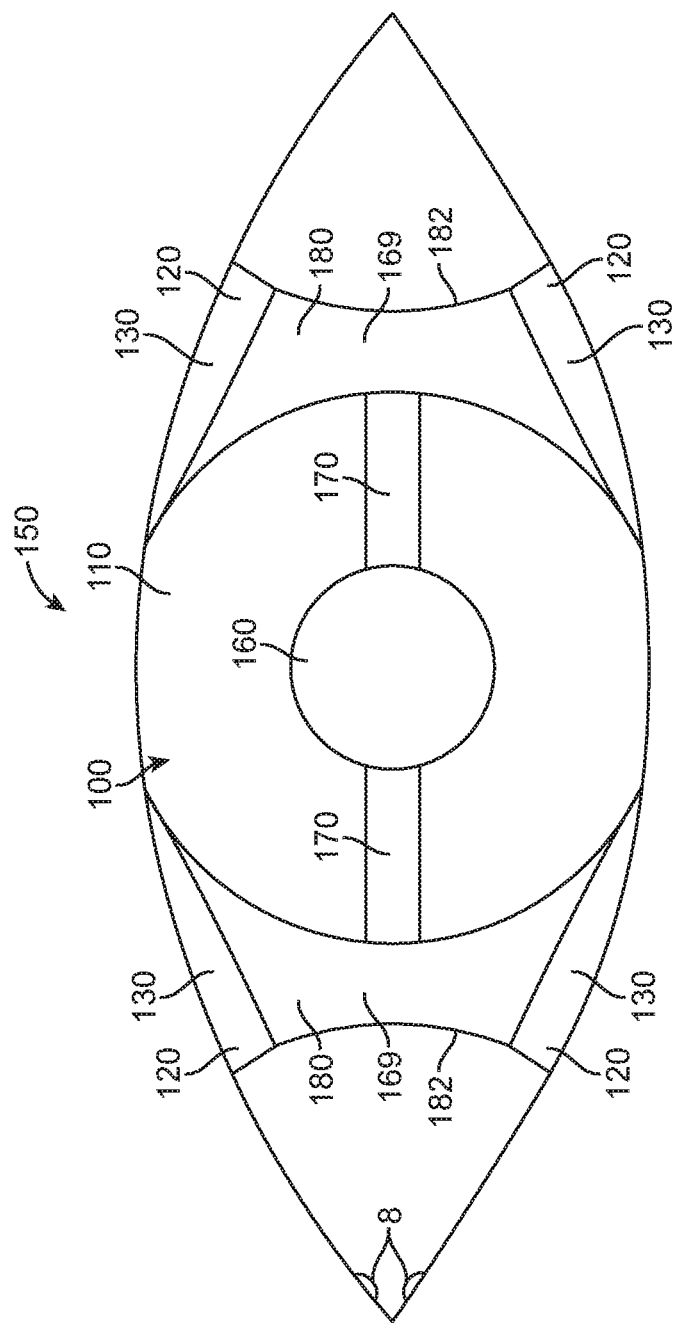
FIG. 2 shows an accommodating contact lens comprising an inwardly curved reservoir wall, in accordance with embodiments.

FIG. 2 shows an accommodating contact lens 100 comprising an inwardly curved reservoir wall 182, in accordance with embodiments. The outer fluid reservoirs 180 of the fluidic module comprise resilient outer walls with an inward curve, such that the curve bows inwards towards the center of the eye when the eyelid fissure narrows and the wing structures 130 of the eyelid engagement structures compress inwards towards the center of the eye. This bowing of the outer reservoir walls can compress the chambers of the outer reservoirs, causing fluid 169 in the reservoirs to move towards the inner, central optical reservoir 160 through the micro-channels in the extensions 170. When the eyelid fissure is widened and the compressive force is released, and the curved outer walls can naturally revert to their unloaded position, drawing the fluid back from the inner optical reservoir to the outer reservoirs.

Figure 3:
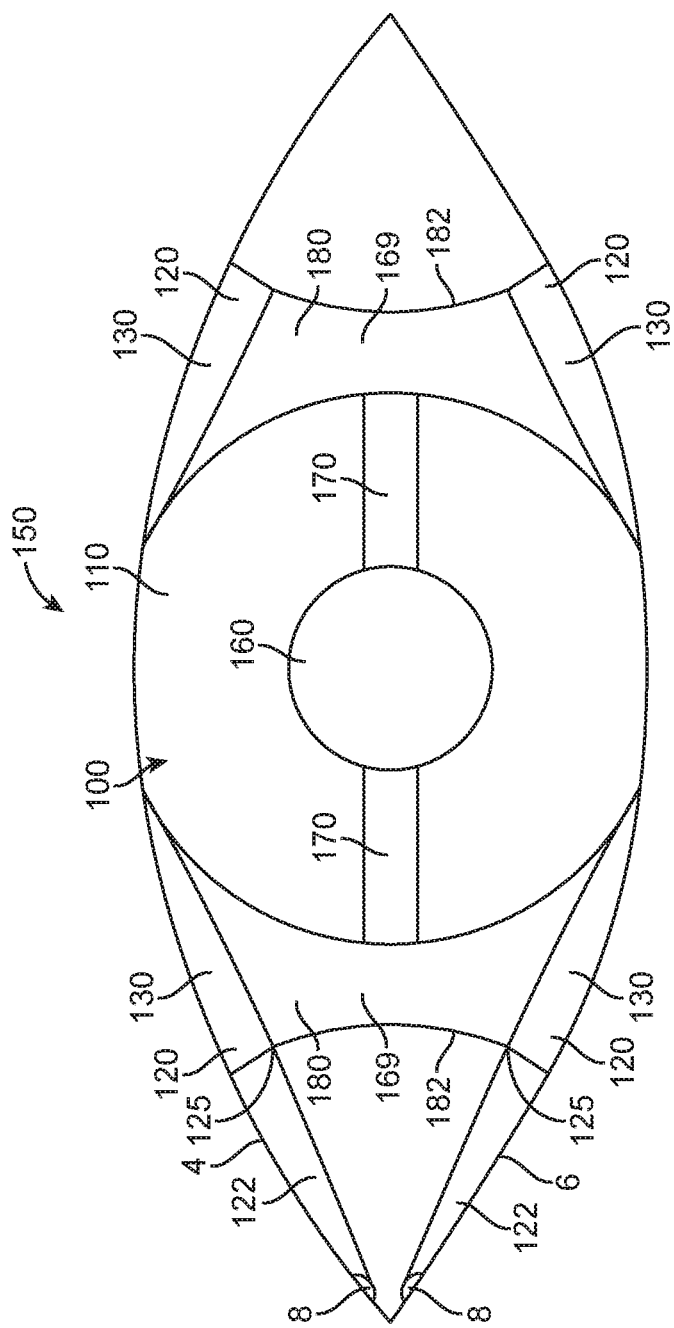
FIG. 3 shows an accommodating contact lens comprising puncta engagement structures, in accordance with embodiments.

FIG. 3 shows an accommodating contact lens 100 comprising puncta engagement structures 122. The contact lens 100 comprises the fluidic module 150 and the eyelid engagement structure 120, and the eyelid engagement structure comprises the puncta engagement structures and wing structures 130. The puncta engagement structures are configured to engage the puncta 8 of the eye, such that the puncta engagement structure engaged to the upper lid engages the upper punctum, and the puncta engagement structured engaged to the lower lid engages the lower punctum. Each puncta engagement structure comprises a length suitably sized to extend to a punctum and may comprise a protrusion sized and shaped to fit within the punctum. The puncta engagement structures and wing structures may be coupled together, such that a force on the puncta engagement structures may be translated to the wing structures and from the wing structures to the outer reservoirs with increased leverage.

When a user squints, a compressive force may be delivered to the puncta engagement structures. The puncta engagement structures may further transmit the force to the wing structures, causing the wing structures to compress the inwardly curved outer walls 182 of the outer reservoir 180. The compressive force may cause the curved outer walls to bow inwards, causing fluid 169 in the outer reservoirs to move into the central optical reservoir 160 to increase the optical power of the central add lens. The puncta engagement structures can allow enhanced user control of the accommodation of the contact lens, since a user may squint in order to generate a higher compressive force on the outer reservoir, thereby increasing the optical power of the central add lens. When the user ceases to squint, the additional compressive force exerted by the squinting is released, allowing at least some of the fluid to move from the inner optical reservoir back to the outer reservoirs and thereby lower the optical power of the central add lens to better accommodate far vision.

Figure 4:
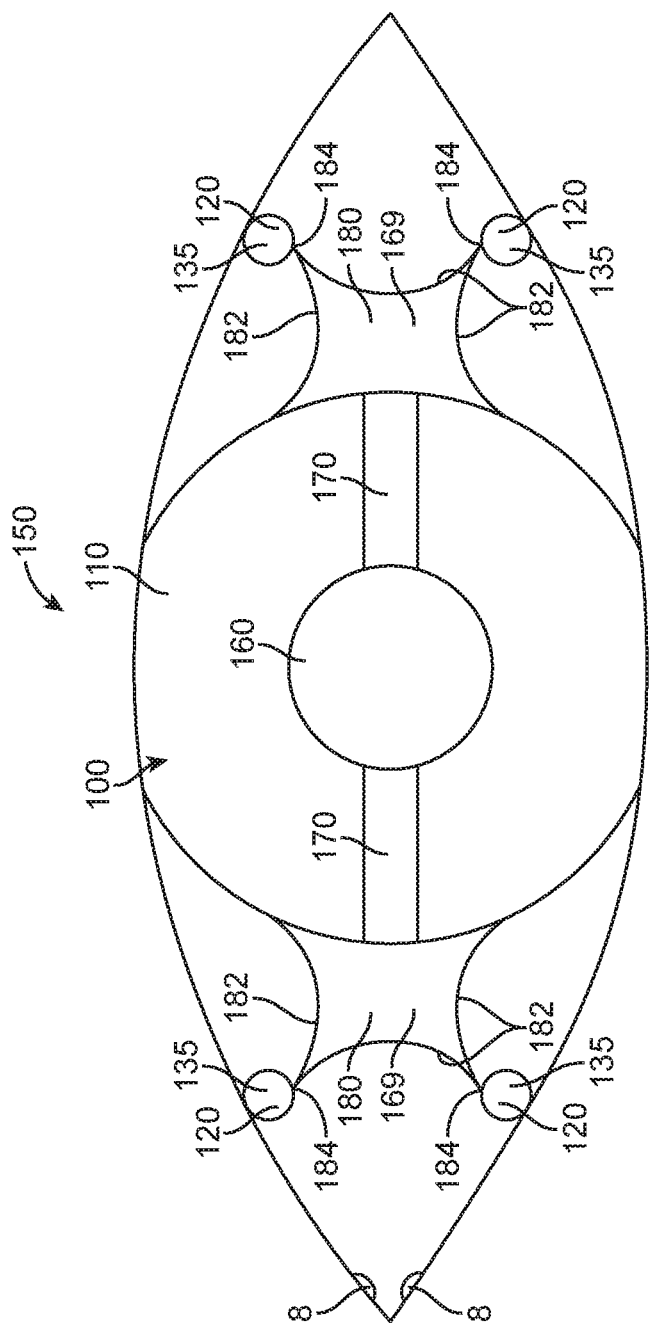
FIG. 4 shows an accommodating contact lens having an eyelid engagement structure, in accordance with embodiments.

FIG. 4 shows an accommodating contact lens 100 having an eyelid engagement structure 120, in accordance with embodiments. The eyelid engagement structure comprises foot plate structures 135, which protrude away from the body of the contact lens. The outer reservoirs 180 of the fluidic module 150 may comprise inwardly curved walls 180 on all three borders not interfacing with the extensions 170.

When the eyelid fissure is narrowed, the foot plate structures compress inwards on the corners 184 of the inwardly curved outer reservoir walls, pushing the corners towards the center of the eye. This compressive force can cause the outer walls to bow inwards, pushing the fluid 169 from the outer reservoirs through channel 170 into the inner optical reservoir 160 and thereby increasing the optical power of the central add lens. When the eyelid fissure widens, the compressive force is released and the fluid may be drawn back into the outer reservoirs from the inner optical reservoir.

FIG. 5 shows a side view of an accommodating contact lens module 150 prior to encapsulation in a soft contact lens material, in accordance with embodiments. The module comprises an inner optical reservoir 160, one or more channels 170, and outer reservoirs 180 having inwardly curved outer walls 182. The inner optical reservoir 160 comprises a top surface 162, bottom surface 166, walls 164, and an inner reservoir chamber 168. The outer reservoirs are coupled to eyelid engagement structures 120 as described herein. The eyelid engagement structure is coupled to an outer reservoir through a coupling structure 126, which may comprise a lever that can move rotationally about the fulcrum 125, in the direction shown by the arrow 129. The narrowing of the eyelid fissure can cause the eyelid engagement structure to move downwards towards the surface of the eye, compressing the inwardly curved wall of the outer reservoir through the lever of the coupling structure. As described herein, the consequent bowing of the outer reservoir wall can compress the chamber of the outer reservoir, causing fluid 169 to move from the outer reservoir into the chamber of the inner optical reservoir. The widening of the eyelid fissure can cause the eyelid engagement structure to return to its unloaded position, releasing the compressive force on the outer reservoir walls and causing fluid to flow from the inner optical reservoir back into the outer reservoirs.

An eyelid engagement structure may comprise one or more of many structures to engage the eyelid. For example, the eyelid engagement structure may comprise an involute structure, a u-shaped structure, a concave structure, or a ball structure. FIG. 6A shows an eyelid engagement structure 120 comprising a protrusion 124, which is formed into a ball-shaped structure. A ball-shaped structure may be an embodiment of a foot plate structure as described herein. FIG. 6B shows an eyelid engagement structure 120 comprising a protrusion 124, which is shaped into an involute structure configured to receive at least a portion of the eyelid. An involute structure may comprise a wing structure or a foot plate structure as described herein. Many other embodiments are contemplated.

The eyelid engagement structure may also comprise one or more of many coupling structures to engage the contact lens. For example, an eyelid engagement structure may comprise a lever, an arm or a slider.

Referring again to FIG. 5, the coupling structure 126 may comprise a lever that exerts a rotational force around the fulcrum 125, so as to exert a compressive force on the outer reservoir.

FIG. 7 shows an eyelid engagement structure 120 comprising a slider structure 128. The eyelid engagement structure 120 may be slidably moveable on the slider structure 128, such that the narrowing of the eyelid fissure causes the eyelid engagement structure to slide towards the center of the eye in order to compress the outer reservoir.

Figure 8:
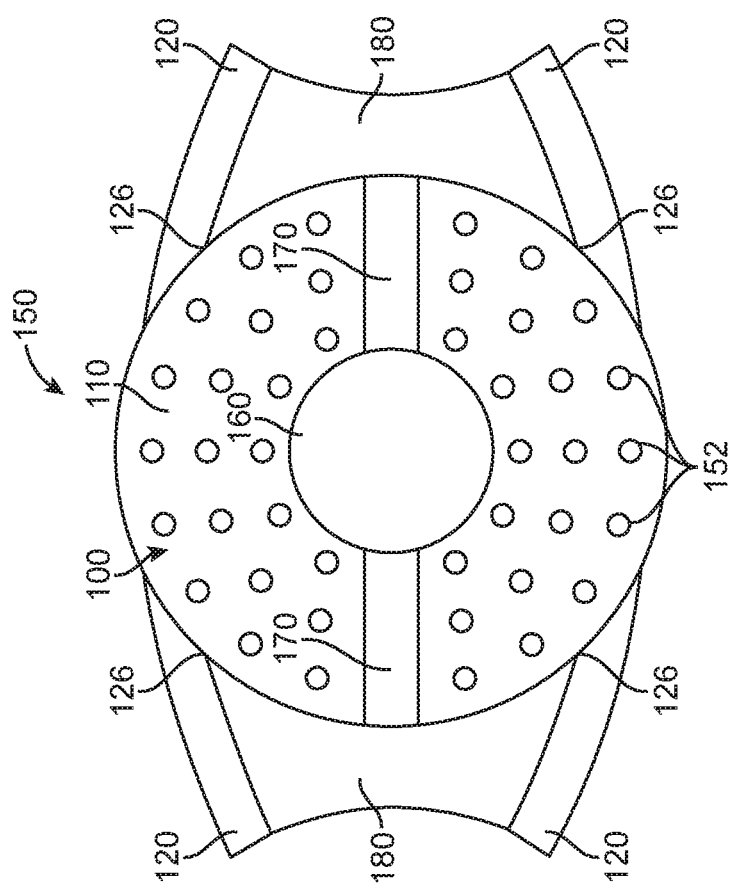
FIG. 8 shows a pre-formed self-supporting module configured for placement in a contact lens mold, in accordance with embodiments.

FIG. 8 shows a pre-formed self-supporting fluidic module 150 configured for placement in a contact lens mold, in accordance with embodiments. In the self-supporting unloaded configuration shown, the module is sized to engage the eyelids. At least a portion of the appropriately sized module can be placed in the mold and used to form the contact lens. The module comprises an optically transmissive material comprising a plurality of anchor structures 152 that can be embedded in a soft contact lens material 110. The module also comprises a coupling structure 126 to couple the eyelid engagement structure 120 with the module, where the coupling structure extends from the reservoir of the module. The self-supporting fluidic module having an inner optical reservoir 160, extensions 170, outer reservoirs 180, and the coupling structures may then be placed in a mold and encapsulated in the soft contact lens material to form the accommodating contact lens 100 as described herein.

The eyelid engagement structure may be configured to allow the eye to blink without triggering the accommodation of the accommodating contact lens. Such a configuration may be a useful feature for when a user may want to blink while looking at distant objects, without having a change in focus. In order to achieve such a configuration, the eyelid engagement structure may be configured to comprise first temporal frequency response characteristics, and the fluidic module may be configured to comprise second frequency response characteristics, such that the first frequency response characteristics comprise frequencies greater than the second frequency response characteristics. The eyelid engagement structure can be coupled to the reservoir with a deflectable member that acts as a spring, for example, and allows rapid movement of the eyelid and only briefly applies pressure to the module with a blink of the eye. For example, one or more channels in the extensions 170 may be coupled to the outer reservoir to release fluid from the channels at a rate slower than the movement of the eyelid in rapid blinking. This differential release rate may allow the eyelid to move quickly with blinks of the eye without moving substantial amounts of fluid from the reservoir and consequently re-adjusting the optical power of the central add lens.

The contact lens may comprise a reservoir of a therapeutic agent coupled to the eyelid engagement structure in order to release amounts of therapeutic agent in response to movement of the eyelid engagement structures. The contact lens can be provided with a release mechanism that releases an amount of therapeutic agent in response to a plurality of inward and outward cycles of the eyelid engagement structure in order to provide an appropriate amount of therapeutic agent. The therapeutic agent may comprise one or more of many known therapeutic agents such as one or more of artificial tears, or glaucoma medication. The reservoir may comprise one or more structures to facilitate pumping with the control device, such as one or more of levers or bellows of the walls of the reservoir, for example.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A contact lens, comprising:
   one or more eyelid engagement structures configured to move with an eyelid relative to at least one other portion of the contact lens; and
   a fluidic module, wherein the fluidic module comprises a coupling structure to couple the eyelid engagement structure with the fluidic module, wherein the coupling structure extends from a support structure of the fluidic module to the eyelid engagement structure and wherein the fluidic module comprises an optically transmissive material comprising a plurality of anchor structures embedded in a soft contact lens material and wherein the fluidic module comprises an outer reservoir and an inner optical reservoir and wherein the fluidic module comprises a self-supporting module comprising the reservoirs and the coupling structure prior to placement in the soft contact lens material.

2. The contact lens as in claim 1, further comprising a control device, wherein the control device is coupled to the one or more eyelid engagement structures in order to control an amount of accommodation of the accommodating contact lens in response to opening and closing of a palpebral fissure of an eye.

3. The contact lens as in claim 1, wherein the one or more eyelid engagement structures is coupled to the outer reservoir of the contact lens with an extension comprising one or more of an arm, a lever, or a wing.

4. The contact lens as in claim 3, wherein the extension is sized to provide leverage to the eyelid engagement structure and decrease resistance to movement of the eyelid engagement structure when eyelids close.

5. The contact lens as in claim 3, wherein the eyelid engagement structure comprises a surface shaped to receive a portion of the eyelid and wherein the extension extends between the outer reservoir and the eyelid engagement structure in order to provide leverage of forces of the eyelid to the reservoir.

6. The contact lens as in claim 3, the extension is coupled to the outer reservoir in order to resiliently deform the reservoir.

7. The contact lens as in claim 1, wherein the eyelid engagement structure comprises a plurality of structures to engage opposing eyelids at a plurality of locations.

8. The contact lens as in claim 1, wherein the eyelid engagement structure is configured to engage one or more puncta of the eye.

9. The contact lens as in claim 1, wherein the eyelid engagement structure comprises a plurality of opposing structures to engage a plurality of eyelids at opposing locations in order to inhibit movement of the lens.

10. The contact lens as in claim 1, wherein the outer reservoir is coupled to the eyelid engagement structure to move a fluid to the inner optical reservoir in response to movement of the eyelid engagement structure with the eyelid.

11. The contact lens as in claim 1, wherein the eyelid engagement structure is coupled to the eyelid with one or more of a ball structure, involute structure, u-shaped structure, or concave structure in order to allow movement of the eyelid engagement structure when the eyelid moves over the contact lens body.

* * * * *